United States Patent
Guillaume et al.

(10) Patent No.: US 6,468,078 B2
(45) Date of Patent: Oct. 22, 2002

(54) IMPRESSION TRAY DEVICE WITH REMOVABLE SEGMENTS FOR DENTAL IMPLANT TRANSFERS

(76) Inventors: Bernard Guillaume, 24 Avenue de Saint-Germain, Maisons Lafitte (FR), 78600; Jean Mazeirat, 147 rue de la Pompe, Paris (FR), 75116

(*) Notice: Subject to any disclaimer, the term of this patent is extended or adjusted under 35 U.S.C. 154(b) by 0 days.

(21) Appl. No.: 09/736,177

(22) Filed: Dec. 15, 2000

(65) Prior Publication Data

US 2001/0010898 A1 Aug. 2, 2001

Related U.S. Application Data

(63) Continuation-in-part of application No. PCT/FR00/00862, filed on Apr. 6, 2000.

(30) Foreign Application Priority Data

Apr. 16, 1999 (FR) .............................. 99 04775

(51) Int. Cl.$^7$ ............................................... A61C 9/00
(52) U.S. Cl. ........................................................ 433/45
(58) Field of Search ............................... 433/37, 38, 41, 433/42, 43, 44, 45 OR, 46, 47, 48

(56) References Cited

U.S. PATENT DOCUMENTS

| 53,347 A | * | 3/1866 | Schaffer | 433/45 |
| 307,579 A | * | 11/1884 | Palmiter | 433/41 |
| 1,489,192 A | * | 4/1924 | Cleveland | 433/45 |
| 3,056,205 A | * | 10/1962 | Ennor | 433/35 |
| 4,708,654 A | | 11/1987 | Branemark | 433/213 |
| 5,336,086 A | * | 8/1994 | Simmen et al. | 433/37 |

FOREIGN PATENT DOCUMENTS

| BE | 568 941 | 12/1960 |
| BE | 569 435 | 5/1961 |

* cited by examiner

Primary Examiner—John J. Wilson
(74) Attorney, Agent, or Firm—Jacobson Holman, PLLC

(57) ABSTRACT

An impression tray for taking impressions of transfers of dental implants comprises, in its closed face, a succession of removable segments secured by screws or by studs. After the impression material has set, the segment(s) giving access to the screw of the transfer is/are removed.

14 Claims, 3 Drawing Sheets

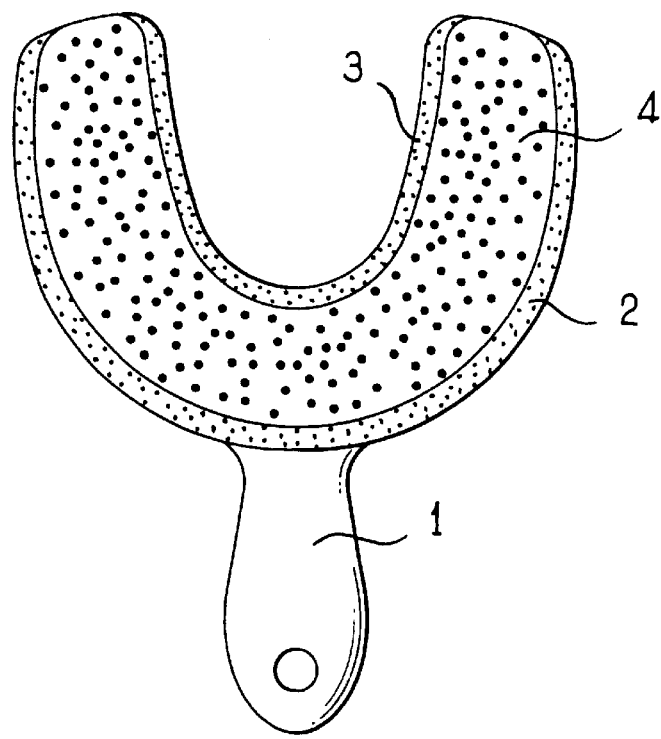
FIG_1
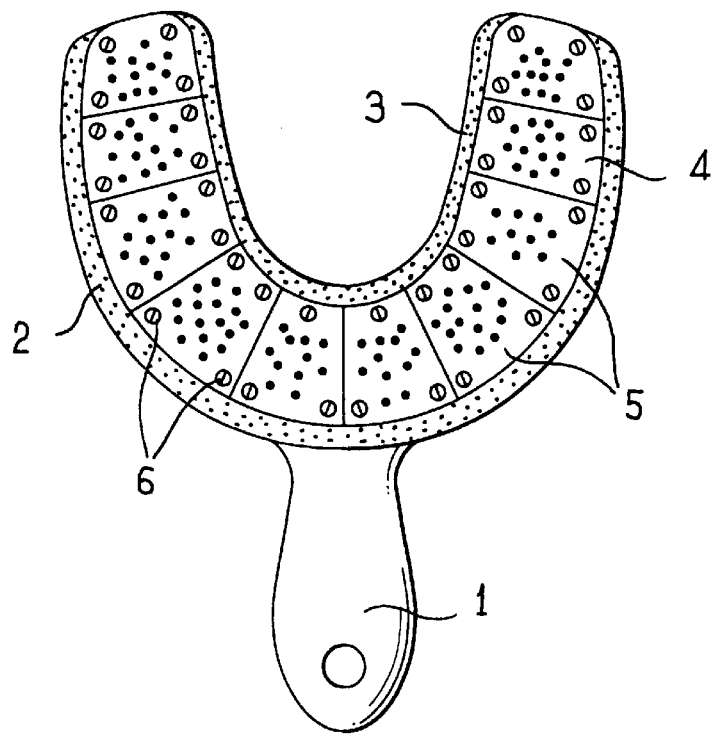
FIG_2

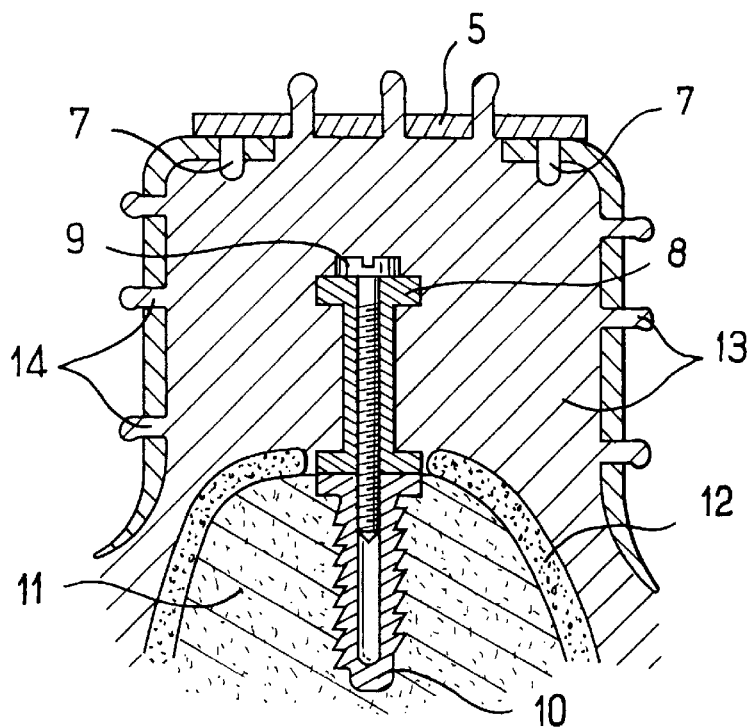
FIG_3
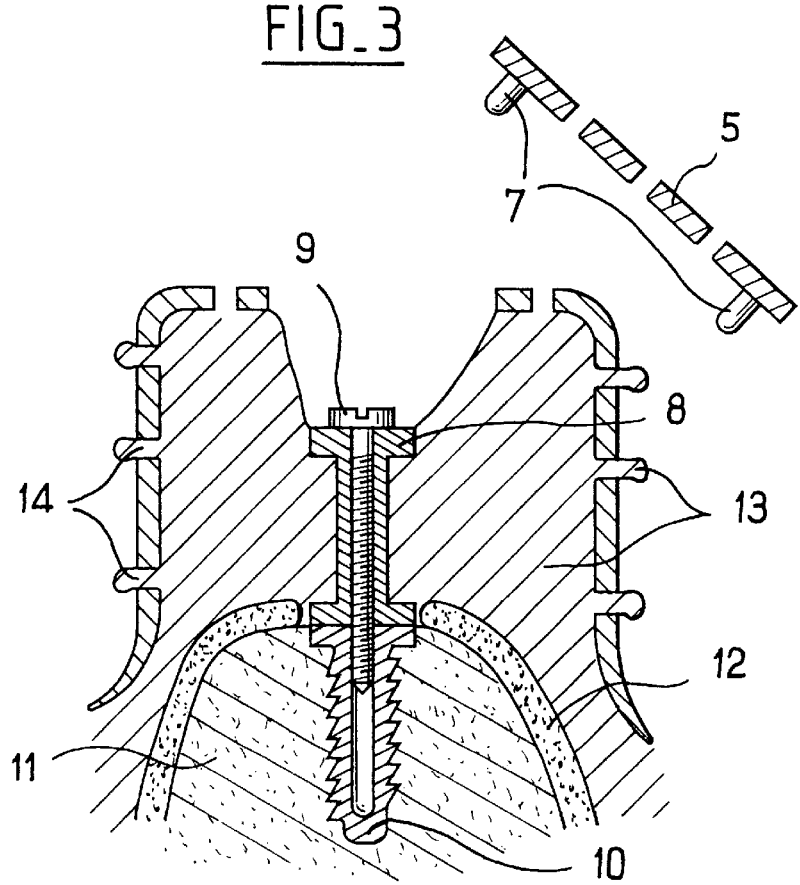
FIG_4

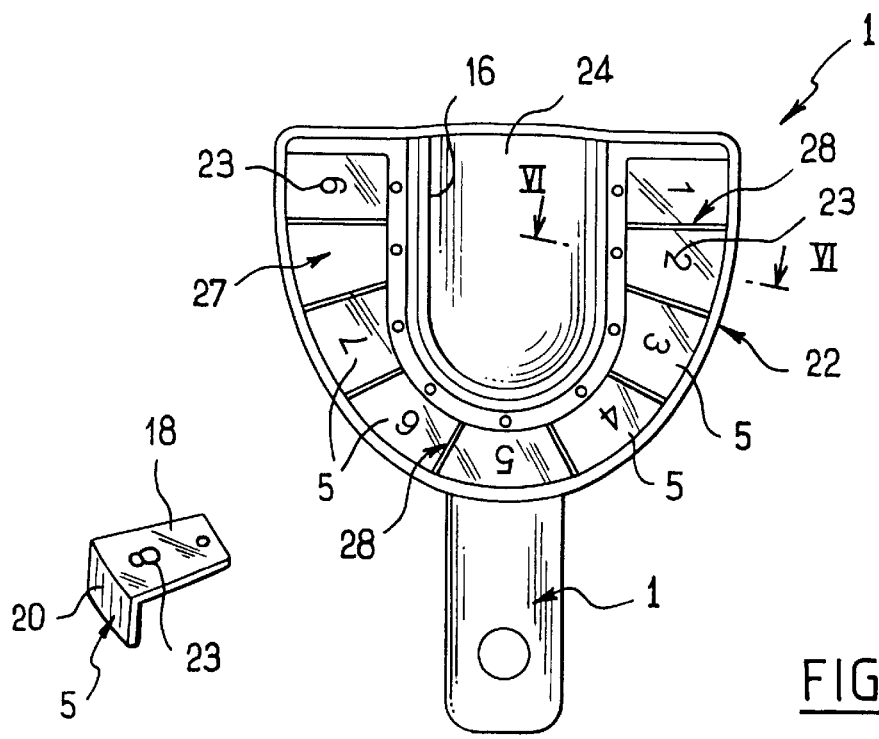
FIG_5
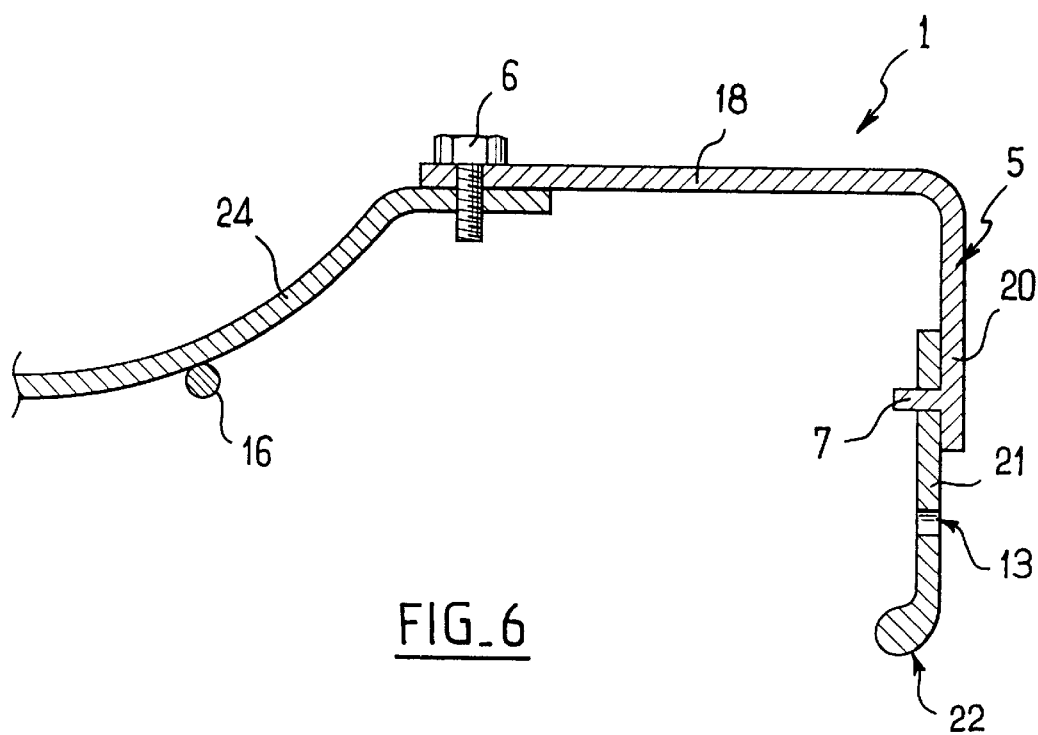
FIG_6

IMPRESSION TRAY DEVICE WITH REMOVABLE SEGMENTS FOR DENTAL IMPLANT TRANSFERS

This application is a continuation-in-part of PCT/FR00/00862 filed on Apr. 6, 2000

BACKGROUND OF THE INVENTION

An implant transfer is a post secured to the implant situated in the dental arch by means of a screw engaged in and tightened in the internal tapping of the implant.

The optionally-perforated conventional impression trays which are used with conjoined or adjoined prostheses cannot be adapted to taking impressions of transfers since they do not have an opening giving access to the screw of the transfer so as to allow the implant to be released, thus enabling the impression to be withdrawn.

OBJECTS AND SUMMARY OF THE INVENTION

The present invention provides an impression tray device for a transfer of a dental implant, in which the tray device has a closed face which includes a succession of removable segments.

BRIEF DESCRIPTION OF THE DRAWINGS

The invention and its implementation will appear more clearly from the following description made with reference to the accompanying drawings showing some embodiments purely by way of example: in the drawings, the same items are identified by the same numbers.

The drawings include the following figures:

FIG. 1 is a plan view of an open face of an impression tray, showing impression material in the tray;

FIG. 2 is a view of the opposite face of the FIG. 1 tray showing segments in its closed wall;

FIG. 3 is a section view through a jaw with an implant and an implant transfer embedded in the impression material in an impression tray;

FIG. 4 is a section view similar to FIG. 3 showing a segment removed together with some impression material to gain access to the transfer;

FIG. 5 is a view of the underside of another embodiment of the impression tray for the upper jaw; and FIG. 6 is a section view on line VI—VI of FIG. 5 through part of the tray.

MORE DETAILED DESCRIPTION

FIG. 1 shows that the impression tray 1 is a semi-elliptical trough having an outer or vestibular face 2, an inner face 3 adjacent to the tongue or the palate, and a closed face 4 corresponding to the grinding surface of the teeth. This impression tray is filled with soft impression material and placed on the dental arch until the material sets.

FIG. 2 shows that in accordance with the invention, the impression tray 1 has a succession of removable segments 5 in its closed face 4 which are secured to the tray 1, in this case by screws 6. One or more of the removable segments 5 can be withdrawn as a function of requirements by loosening the screws 6.

FIG. 3 is a cross-section through the device of the invention. In this embodiment, the removable segments 5 are secured to the tray 1 by studs 7. The section plane contains the axis of the studs 7, the axis of the transfer 8, the axis of the screw 9 which secures the transfer 8 to the implant 10, and finally the axis of the implant 10 situated in the bone 11 which is covered by the gum 12.

The assembly comprising the impression tray 1 and the transfer 8 is held together by the impression material 13 which oozes out through holes 14 in the tray 1 so as to hold the material 13 relative to the tray.

FIG. 4 shows how access is gained to the screw 9, after the impression material 13 has set, once the removable segment 5 is taken away, and after a small amount of impression material 13 has been removed.

FIGS. 5 and 6 show a variant embodiment of the impression tray of the invention.

FIG. 5 is a view from beneath of an impression tray for the upper jaw with one of the removable segments removed and shown separately, and FIG. 6 is a section through said tray on plane VI—VI of FIG. 5.

In this variant, each removable segment 5 is fixed to the tray by means of a screws 6 and a stud 7. Each segment is of L-shaped profile. One branch of the L-shape forms a plane wall 18 forming a closing face that corresponds to the grinding face of the teeth. The other branch of the L-shape forms a plane outer side wall 20 corresponding to a part of the outer or vestibular face of the tray. These two walls are substantially perpendicular to each other. In a varying embodiment, these two walls could form a slightly obtuse angle.

The tray is open in register with the two walls 18 and 20 for each removable segment 5 and the segment closes this opening. The wall 18 is fixed to the tray by means of the screw 6 situated close to the edge of the wall remote from the wall 20. The wall 20 is fixed to the tray by means of the stud 7 situated close to the edge of the wall remote from the wall 18.

The peripheral outer wall 21 of the tray presents an elongate end edge 22 with reinforcing extra thickness protruding internally all around the tray. This thickness improves the holding of the impression material in the tray.

Whereas the tray of FIG. 2 which corresponds to the lower jaw has an open center, the tray of FIGS. 5 and 6 corresponding to the upper jaw has a wall 24 for matching the shape of the patient's palate. In this case, the palate wall is reinforced by a rib or swelling 16 that is generally U-shaped in plane and that extends past all of the removable segments 5. This rib 16 too improves the holding of the impression material in the tray.

As shown on FIG. 5, each removable segment shows a distinctive reference mark 23. In instant case, the removable segments are numbered from 1 to 9, with the segment number 8 removed and showed separately, leaving an empty place 27 on the tray. As the segments all have different shapes, these references help to put the segments back on the tray at their right places. Beside, the adjacent removable segments 5 on the tray are separated by a gap 28 for allowing the impression material to ooze out or flow therethrough when taking the impression and for holding the material in the tray. The peripheral wall 21 of the tray has orifices 13 for allowing the impression material to ooze out or flow therethrough and for holding the material in the tray. These flowings also permit to evacuate the forces exerted on the tray during the taking of the impression.

With this tray also, the method of taking an impression of a dental arch including an implant transfer fixed to a dental implant by means of a screw, comprises the steps consisting in:

removing the removable segment that is aimed to extend in register with the transfer;

taking the impression by means of the tray filled with impression material, allowing the impression material to harden;

removing the screw in view of separating the transfer from the implant; and removing the impression tray with the transfer incorporated in the impression material.

What is claimed is:

1. An impression tray device for a transfer of a dental implant, the tray device comprising:

a body having a closed face; and a succession of segments removable from the body, each segment having two walls forming an L-shaped profile of the segment, the body having an opening extending in register with each of the walls so that each wall of the segments substantially closes the opening.

2. The device of claim 1, in which the removable segments are secured to the impression tray by screws.

3. The device of claim 1, in which the removable segments are secured to the impression tray by studs.

4. The device of claim 1, in which each removable segment is secured to the tray by means of at least one stud and at least one screw.

5. The device of claim 1, in which one branch of the L-shape occupies an outer side face of the device.

6. The device of claim 1, in which a central zone of the device has a through opening.

7. The device of claim 1, in which a central zone of the device presents a wall.

8. The device of claim 7, in which the wall of the central zone presents a reinforcing rib which is U-shaped in a plane.

9. The device of claim 1, in which an elongate terminal edge of the device presents an extra thickness for holding impression material.

10. The device of claim 1, in which the removable segments have reference marks.

11. The device of claim 1, in which two removable segments adjacent one from the other on the tray are separated one from the other by a gap.

12. The impression tray device as claimed in claim 1, wherein the segments have holes for filling with cast material.

13. The impression tray device as claimed in claim 1, wherein the segments cover an exterior of the body.

14. A method of taking an impression of a dental arch including an implant transfer fixed to a dental implant by a screw, the method comprising the steps of:

locating a succession of removable segments on an impression tray in a closed face;

removing one of the removable segments that is aimed to extend in register with the transfer;

taking the impression by the tray filled with impression material;

allowing the impression material to harden;

removing the screw in view of separating the transfer from the implant; and removing the impression tray with the transfer incorporated in the impression material.

* * * * *